"

US010119963B2

(12) United States Patent
Takahashi et al.

(10) Patent No.: US 10,119,963 B2
(45) Date of Patent: Nov. 6, 2018

(54) PSA ASSAY AND REAGENT THEREFOR

(71) Applicant: SEKISUI MEDICAL CO., LTD., Tokyo (JP)

(72) Inventors: Yuki Takahashi, Ryugasaki (JP); Tomo Shimizu, Ryugasaki (JP); Yasushi Nakamura, Ryugasaki (JP); Shinya Nakayama, Ryugasaki (JP); Shinichiro Kitahara, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 29 days.

(21) Appl. No.: 14/865,728

(22) Filed: Sep. 25, 2015

(65) Prior Publication Data
US 2016/0011181 A1    Jan. 14, 2016

Related U.S. Application Data

(63) Continuation of application No. 14/008,441, filed as application No. PCT/JP2012/058056 on Mar. 28, 2012.

(30) Foreign Application Priority Data

Mar. 28, 2011 (JP) .................................. 2011-069161

(51) Int. Cl.
G01N 33/543    (2006.01)
G01N 33/574    (2006.01)
G01N 33/573    (2006.01)
G01N 33/577    (2006.01)

(52) U.S. Cl.
CPC ......... *G01N 33/543* (2013.01); *G01N 33/573* (2013.01); *G01N 33/577* (2013.01); *G01N 33/57434* (2013.01); *G01N 2333/96433* (2013.01)

(58) Field of Classification Search
CPC .................................................. G01N 33/573
See application file for complete search history.

(56) References Cited

U.S. PATENT DOCUMENTS

| 5,185,264 A * | 2/1993 | Makela ................. G01N 33/50 422/527 |
| 8,026,107 B2 | 9/2011 | Yoshida et al. |
| 8,722,342 B2 | 5/2014 | Yamamoto et al. |
| 8,987,005 B2 | 3/2015 | Yamamoto et al. |
| 2004/0157276 A1 | 8/2004 | Sumida et al. |
| 2005/0069967 A1 | 3/2005 | Sumida et al. |
| 2008/0044926 A1 | 2/2008 | Honjo et al. |
| 2009/0263915 A1 | 10/2009 | Yoshida et al. |
| 2010/0167310 A1 | 7/2010 | Yamamoto et al. |
| 2011/0104825 A1 | 5/2011 | Yamamoto et al. |
| 2011/0236996 A1 | 9/2011 | Nakayama et al. |
| 2014/0377881 A1 | 12/2014 | Kitahara et al. |
| 2015/0080542 A1 | 3/2015 | Kitahara et al. |
| 2015/0233906 A1 * | 8/2015 | Kitahara ................. C08L 33/14 524/547 |

FOREIGN PATENT DOCUMENTS

| CN | 101088010 A | 12/2007 |
| CN | 101351707 A | 1/2009 |
| CN | 101517412 A | 8/2009 |
| JP | 10-123137 A | 5/1998 |
| JP | 2001-108681 A | 4/2001 |
| JP | 2005-106609 A | 4/2005 |
| JP | 2007-163319 A | 6/2007 |
| JP | 2007163319 A * | 6/2007 |
| WO | WO 2006/068206 A1 | 6/2006 |
| WO | WO 2010/001619 A1 | 1/2010 |
| WO | WO 2010/064435 A1 | 6/2010 |

OTHER PUBLICATIONS

Andersson et al., "Antibody-antigen interactions: What is the required time to equilibrium?", Nov. 10, 2010 (6 pages total), Available from Nature Precedings <http://hdl.handle.net/10101/npre.2010.5218. 1>.*
Chinese Office Action and Search Report for Chinese Application No. 201510964173.X, dated Sep. 26, 2016, with an English translation of the Office Action only.
Corey, et al, "Characterization of 10 New Monoclonal Antibodies Against Prostate-Specific Antigen by Analysis of Affinity, Specificity and Function in Sandwich Assays," International Journal Cancer, 1997, vol. 71, pp. 1019-1028.
English translation of International Preliminary Report on Patentability and Written Opinion dated Oct. 10, 2013, in PCT International Application No. PCT/JP2012/058056.
Extended European Search Report dated Nov. 19, 2014, in European Patent Application No. 12763300.6.
International Search Report issued in PCT/JP2012/058056 dated Apr. 24, 2012.

(Continued)

Primary Examiner — Tracy Vivlemore
Assistant Examiner — Nam P Nguyen
(74) Attorney, Agent, or Firm — Birch, Stewart, Kolasch & Birch, LLP

(57) ABSTRACT

Provided is a method for the simple and highly accurate assay of PSA by a one-step reaction that does not use carriers having different average grain sizes. Also provided is a reagent therefor. The PSA assay method comprises sensitizing insoluble carriers having the same average grain size within a range of greater than 0.20 µm but 0.40 µm or less using two types of anti-PSA monoclonal antibodies having different epitopes that are anti-PSA monoclonal antibodies that will react with both free PSA and PSA-ACT, which is a complex of free PSA and α1-antichymotrypsin, and bringing the carriers into contact with a sample in the presence of an aggregation promoter.

11 Claims, No Drawings

(56) References Cited

OTHER PUBLICATIONS

Xie et al., "Development of Simultaneous Detection of Total Prostate-Specific Antigen (tPSA) and Free PSA with Rapid Bead-Based Immunoassay," Journal of Clinical Laboratory Analysis (2011), vol. 25, pp. 37-42.

* cited by examiner

PSA ASSAY AND REAGENT THEREFOR

CROSS REFERENCE TO RELATED APPLICATIONS

This application is a Continuation of U.S. application Ser. No. 14/008,441, filed Dec. 4, 2013. U.S. application Ser. No. 14/008,441 is the National Phase of PCT/JP2012/058056 filed on Mar. 28, 2012, which claims priority under 35 U.S.C. 119(e) to Patent Application No. 2011-069161 filed in Japan on Mar. 28, 2011, all of which are hereby expressly incorporated by reference into the present application.

TECHNICAL FIELD

The invention relates to an antigen assay and a reagent that make it possible to measure a free antigen, and a complex of a free antigen and a coexisting substance in a sample, by immune agglutination so that an equimolar response is obtained. In particular, the invention relates to an assay of prostate-specific antigen, and a reagent therefor.

BACKGROUND ART

Prostate cancer is a malignant disease that is observed in men. A large number of patients suffer from prostate cancer in the United States and Europe. In recent years, the number of patients who suffer from prostate cancer has rapidly increased in Japan. Since prostate cancer grows slowly, and may effectively be treated by radiotherapy or anti-androgenic therapy, it is important to find prostate cancer in an early stage.

Prostate-specific antigen (hereinafter may be referred to as "PSA") is a glycoprotein (serine protease) that is secreted from prostate epithelial cells, and has a molecular weight of 33,000 to 34,000 Da. Since a person who suffers a prostate disease shows an increase in PSA level in blood as compared with a healthy person, PSA is useful for early detection of a prostatic disease (particularly prostate cancer). PSA is classified into complex-type PSA that binds to a protease inhibitor in blood, and free PSA (hereinafter may be referred to as "fPSA"). Most of the PSA in blood is complex-type PSA, and present as complex of PSA and α1-antichymotrypsin (hereinafter may be referred to as "PSA-ACT"), complex of PSA and α2-macroglobulin, or the like. fPSA and PSA-ACT can be measured by an immunoassay.

An assay based on agglutination (immunoagglutination assay) that utilizes a latex or the like is used as the immunoassay. However, since an anti-PSA monoclonal antibody has different reactivity with fPSA and PSA-ACT, it may be difficult to accurately measure the total PSA level.

In order to solve the above problem, PTL 1 proposes an immunoagglutination assay reagent and an assay that utilizes the same, wherein the immunoagglutination assay reagent including (1) a first particle suspension that includes first insoluble carrier particles immobilizing thereon a first monoclonal antibody that can bind to a free measurement target substance and a complex of the free measurement target substance and the corresponding binding molecule, (2) a second particle suspension that includes second insoluble carrier particles immobilizing thereon a second monoclonal antibody that can bind to the free measurement target substance and a complex of the free measurement target substance and the corresponding binding molecule, and does not compete with the first monoclonal antibody, and (3) a third particle suspension that includes third insoluble carrier particles immobilizing thereon a third monoclonal antibody that does not recognize the free measurement target substance, but recognizes a complex of the free measurement target substance and the corresponding binding molecule.

PTL 2 proposes an assay reagent and an assay that utilizes the same, wherein the assay reagent adjusting reactivity with a free antigen and a complex-type antigen by using carriers having a smaller particle size among two or more types of carriers that differ in particle size and immobilizing thereon at least one monoclonal antibody among three monoclonal antibodies that have reactivity with a free antigen and a complex-type antigen and differ in recognition site, and using carriers having a larger particle size among the two or more types of carriers and immobilizing thereon the remaining monoclonal antibodies.

PTL 3 proposes a two-step reaction immunoassay that includes (1) reacting a sample that includes a free measurement target substance and a complex-type measurement target substance with a latex 1 on which a monoclonal antibody 1 to the measurement target substance is immobilized to obtain a reaction product 1, and (2) reacting the reaction product 1 with a latex 2 on which a monoclonal antibody 2 that differs in recognition site from the monoclonal antibody 1 is immobilized to obtain a reaction product 2.

PTL 4 proposes a prostate-specific antigen immunoassay reagent and an assay that utilizes the same, wherein the immunoassay reagent including a latex 1 on which a monoclonal antibody 1 that has reactivity with free PSA and PSA complex is immobilized, and a latex 2 on which a monoclonal antibody 2 that has reactivity with free PSA and PSA complex is immobilized, the monoclonal antibody 2 differing in recognition site from the monoclonal antibody 1, and the latex 2 differing in average particle size from the latex 1.

CITATION LIST

Patent Literature

PTL 1: JP-A-2001-108681
PTL 2: WO2006/068206
PTL 3: JP-A-2007-163319
PTL 4: Japanese Patent No. 4241301

SUMMARY OF INVENTION

Technical Problem

However, when using the method disclosed in PTL 1, a decrease in relative measured value is observed as the mixing ratio of PSA-ACT increases (see the measurement results when a polystyrene latex having an average particle size of 0.78 μm and immobilizing an anti-PSA monoclonal antibody thereon, and fPSA and PSA-ACT are mixed in a different ratio). Specifically, when only PSA-ACT is used, the relative measured value to free PSA is 81.43% and an equimolar response is not obtained. The method disclosed in PTL 2 has a problem in that it is necessary to combine latexes that differ in particle size, and the method disclosed in PTL 3 has a problem in that it is necessary to employ a two-step reaction in which the second monoclonal antibody is reacted after reacting the first monoclonal antibody. The method disclosed in PTL 4 also has a problem in that it is necessary to combine latexes that differ in particle size. PTL 4 discloses a comparative example in which latexes having an identical average particle size (0.22 μm) are used. However, an agglutination accelerator is not used, and an equimolar response is not obtained.

In view of the above situation, development of a method that can more easily and accurately measure the total PSA level (i.e., the sum of fPSA and PSA-ACT that can be measured by an immunoassay) has been desired.

Specifically, an object of the invention is to provide an assay that easily and accurately measures PSA by a one-step reaction without using carriers that differ in average particle size, and a reagent used therefor. Note that the expression "measurement of PSA" or "assay of PSA" used herein refers to measurement or assay of the total PSA level unless otherwise specified.

Solution to Problem

Several aspects of the invention that achieve the above object include the following.
(1) A PSA assay comprising using insoluble carriers immobilizing thereon two kinds of anti-PSA monoclonal antibodies, and bringing the insoluble carriers into contact with a sample in the presence of an agglutination accelerator, wherein the two kinds of anti-PSA monoclonal antibodies can react with both free PSA and complex of free PSA and α1-antichymotrypsin (PSA-ACT) and recognize different epitopes, and the insoluble carriers have an identical average particle size that is more than 0.20 µm and equal to or less than 0.40 µm.
(2) The PSA assay according to (1), wherein the agglutination accelerator is one or more agglutination accelerators selected from polyethylene glycol, a polysaccharide, polyvinylpyrrolidone, polyvinyl chloride, a poly-γ-glutamate, and poly(2-methacryloyloxyethylphosphorylcholine).
(3) The PSA assay according to (1), wherein the insoluble carriers are of one or more type selected from particles comprising materials derived from latex particles of synthetic polymers, silica, alumina, carbon blacks, metal compounds, metals, ceramics, and/or magnetic substances.
(4) The PSA assay according to (1), wherein the concentration of the agglutination accelerator is adjusted so that an equimolar response to free PSA and complex of free PSA and α1-antichymotrypsin (PSA-ACT) is obtained.
(5) The PSA assay according to (2), wherein the polysaccharide is one or more polysaccharides selected from dextran, pullulan, and alkylated polysaccharides including methyl cellulose and ethyl cellulose.
(6) The PSA assay according to (3), wherein the synthetic polymer is one or more synthetic polymers selected from polystyrene, a styrene-sulfonic acid copolymer, a styrene-methacrylic acid copolymer, an acrylonitrile-butadiene-styrene copolymer, a vinyl chloride-acrylate copolymer, and a vinyl acetate-acrylate copolymer.
(7) The PSA assay according to any one of (1) to (6), wherein each of the two kinds of anti-PSA monoclonal antibodies has a ratio (fKd/cKd) of a dissociation constant (fKd) for free PSA to a dissociation constant (cKd) for complex of free PSA and α1-antichymotrypsin (PSA-ACT) of more than 0.1 and equal to or less than 2.0, and has a dissociation constant (fKd) for free PSA of 10 nM or less.
(8) A PSA assay reagent comprising at least 1) and 2):
1) antibody-immobilized carriers prepared by using insoluble carriers immobilizing thereon two kinds of anti-PSA monoclonal antibodies, wherein the two kinds of anti-PSA monoclonal antibodies can react with both free PSA and complex of free PSA and α1-antichymotrypsin (PSA-ACT) and recognize different epitopes, and the insoluble carriers have an identical average particle size that is more than 0.20 µm and equal to or less than 0.40 µm; and/or
2) one or more agglutination accelerators selected from polyethylene glycol, a polysaccharide, polyvinylpyrrolidone, polyvinyl chloride, a poly-γ-glutamate, and poly(2-methacryloyloxyethylphosphorylcholine).
(9) The PSA assay according to (1), wherein each of the two kinds of anti-PSA monoclonal antibodies has a ratio (fKd/cKd) of a dissociation constant (fKd) for free PSA to a dissociation constant (cKd) for complex of free PSA and α1-antichymotrypsin (PSA-ACT) of more than 0.1 and equal to or less than 2.0 and has a dissociation constant (fKd) for free PSA of 10 nM or less, the agglutination accelerator is one or more agglutination accelerators selected from polyethylene glycol, a polysaccharide, polyvinylpyrrolidone, polyvinyl chloride, a poly-γ-glutamate, and poly(2-methacryloyloxyethylphosphorylcholine), and the amount of the agglutination accelerator is adjusted so that an equimolar response to free PSA and complex of free PSA and α1-antichymotrypsin (PSA-ACT) is obtained.

Advantageous Effects of Invention

The assay according to the aspect of the invention can easily and accurately measure PSA by a one-step reaction without using carriers that differ in average particle size. Therefore, it is possible to implement high-accuracy measurement using a general-purpose automatic analyzer without requiring a special device.

DESCRIPTION OF EMBODIMENTS (Measurement Target Substance)
The embodiments of the invention are targeted at prostate-specific antigen (PSA) (i.e., measurement target substance). PSA in plasma that can be measured by immunoassay include free PSA (fPSA) and complex of free PSA (fPSA) and α1-antichymotrypsin (PSA-ACT).

The target sample is not particularly limited as long as the sample includes PSA, but is preferably blood, serum, plasma, or the like.
(Anti-PSA Monoclonal Antibody)
At least two kinds of anti-PSA monoclonal antibodies that can react with both fPSA and PSA-ACT and recognize different epitopes are used as monoclonal antibodies to PSA. The difference in epitope between the two kinds of anti-PSA monoclonal antibodies can be determined by confirming whether normal sandwich immunoassay using PSA (antigen) and these antibodies is possible or not.
(Selection of Antibodies)
The antibodies are selected as described below.

It is desirable to select an antibody that has high reactivity (i.e., high titer) with PSA-ACT and fPSA by ELISA or the like. It is desirable to select carriers that ensure sufficient measurement sensitivity. The carriers immobilize thereon two kinds of antibodies arbitrarily selected from the antibodies selected to have a high titer, and a combination of antibodies are selected so that the reactivity with PSA-ACT and fPSA shows small difference and sufficient measurement sensitivity is obtained.

It is preferable that the anti-PSA monoclonal antibodies have a ratio (fKd/cKd) of the dissociation constant (fKd) for free PSA to the dissociation constant (cKd) for complex of free PSA and α1-antichymotrypsin (PSA-ACT) of more than 0.1, and more preferably more than 0.2. The upper limit of the ratio (fKd/cKd) is preferably 2.0 or less, and more preferably 1.5 or less. The dissociation constant (fKd) for free PSA is preferably 10 nM or less, and more preferably 6 nM or less.

The monoclonal antibodies may include, for example, an Fab fragment obtained by partial hydrolysis by papain or the like, an F(ab')$_2$ fragment obtained by partial hydrolysis by pepsin or the like, and/or an Fab' fragment obtained by reduction of an F(ab')$_2$ fragment.

(Insoluble Carriers)

The insoluble carriers immobilizing antibodies thereon are not particularly limited, but are preferably selected from particles comprising materials derived from latex particles of synthetic polymers, silica, alumina, carbon blacks, metal compounds, metals, ceramics, and/or magnetic substances. The synthetic polymer is preferably one or more synthetic polymers selected from polystyrene, a styrene-sulfonic acid copolymer, a styrene-methacrylic acid copolymer, an acrylonitrile-butadiene-styrene copolymer, a vinyl chloride-acrylate copolymer, and a vinyl acetate-acrylate copolymer.

It is particularly preferable to use particles of a polystyrene latex obtained by soap-free emulsion polymerization. The polystyrene latex may be produced, for example, by the method disclosed in WO2003/005031. Specifically, a reaction vessel containing water as a solvent is charged with specific amounts of a styrene monomer, an initiator (e.g., potassium persulfate), and a polymerization stabilizer (e.g., sodium styrene sulfonate). After optionally adding emulsifier (e.g., sodium lauryl sulfate), the mixture is heated with stirring in a nitrogen atmosphere to effect polymerization.

(Particle Size of Insoluble Carriers)

The average particle size of the insoluble carriers is more than 0.20 μm and equal to or less than 0.40 μm, preferably more than 0.22 μm and equal to or less than 0.40 μm, more preferably equal to or more than 0.23 and equal to or less than 0.40 μm, and still more preferably equal to or more than 0.23 and equal to or less than 0.34 μm. If the average particle size of the insoluble carriers is 0.20 μm or less, or exceeds 0.40 μm, it may be difficult to obtain an equimolar response. Note that the term "average particle size (μm)" used herein in connection with the insoluble carriers refers to a value that is obtained by image analysis using a transmission electron microscope (see the examples) and rounded off to two decimal places. Note that the average particle size can be calculated to four decimal places by image analysis.

In case that the average particle size is more than 0.20 μm and equal to or less than 0.40 μm, it is considered that two types of particles (e.g. prepared in different lots) have an identical average particle size when the average particle sizes of the two types of particles satisfy the relationship "M-N≤P+Q" when the average particle size (±SD) of particles A is M±N, the average particle size (±SD) of particles B is P±Q, M>P, and N and Q are 0.02 μm or less.

For example, when the average particle size of particles A is 0.22±0.02 μm and the average particle size of particles B is 0.21±0.02 μm, M-N is 0.20 and P+Q is 0.23 (i.e., the above relationship is satisfied). Therefore, it is considered that the particles A and the particles B have an identical average particle size.

When the average particle size of particles A is 0.40±0.02 μm and the average particle size of particles B is 0.37±0.02 μm, M-N is 0.38 and P+Q is 0.39 (i.e., the above relationship is satisfied). Therefore, it is considered that the particles A and the particles B have an identical average particle size.

A mixture of particles wherein the particles are considered to have an identical average particle size as mentioned above and are mixed in an arbitrary ratio is within the scope of the invention.

According to the embodiments of the invention, two or more carriers have an identical average size, but a combination of carriers made from different materials is not excluded. A combination of carriers having different average particle sizes is also not excluded, as long as the carrier therefrom has an average particle size within the above range and is used in the main reaction to obtain an equimolar response.

(Immobilization of Antibodies)

The insoluble carriers may immobilize the antibodies thereon by a generally-used physical adsorption method, and a chemical binding method, an immunobinding method, or the like is used as well. The carriers which have respectively immobilize thereon two kinds of monoclonal antibodies that recognize different epitopes are normally mixed in an appropriate ratio (see the examples), but the two kinds of monoclonal antibodies may be mixed beforehand in an appropriate ratio to be immobilized on the carriers.

(Agglutination Accelerator)

The agglutination accelerator is not particularly limited as long as the agglutination accelerator promotes agglutination of the insoluble carriers that immobilize the antibodies thereon via an antigen-antibody reaction. Examples of the agglutination accelerator include polyethylene glycol, a polysaccharide, polyvinylpyrrolidone, polyvinyl chloride, a poly-γ-glutamate, poly(2-methacryloyloxyethylphosphorylcholine) (hereinafter may be referred to as "MPC polymer"), and the like. The polysaccharide is preferably one or more polysaccharides selected from dextran, pullulan, and alkylated polysaccharides including methyl cellulose and ethyl cellulose. The poly-γ-glutamate may be an alkali metal salt (e.g., sodium, potassium, or lithium salt), an alkaline-earth metal salt (e.g., magnesium, calcium, or barium salt), or an ammonium salt.

Among these, polyethylene glycol and polyvinylpyrrolidone are preferable, and polyethylene glycol is more preferable. Note that a plurality of agglutination accelerators may be used in combination.

Products that differ in molecular weight are commercially available as the agglutination accelerator, and may be appropriately selected taking account of water-solubility and the like. The number average molecular weight of polyethylene glycol is preferably 3,000 to 1,000,000, for example, more preferably 5,000 to 100,000, and particularly preferably 5,000 to 50,000. When the number average molecular weight of polyethylene glycol is 3,000 to 1,000,000, excellent measurement sensitivity can be achieved. Polyvinylpyrrolidone may have a weight average molecular weight of 25,000 to 1,200,000, for example, and preferably 40,000 to 360,000. The poly-γ-glutamate may have a weight average molecular weight of 200,000 to 6,000,000, for example. The MPC polymer may have a molecular weight of 5,000 to 5,000,000, for example, and preferably 500,000 to 2,000,000.

It is preferable to appropriately set the concentration of the agglutination accelerator so that an equimolar response is obtained taking account of the average particle size of the carriers and the type of the agglutination accelerator. For example, the concentration of the agglutination accelerator is preferably adjusted so that the final concentration of the agglutination accelerator is 0.1 to 5 wt %, more preferably 0.2 to 2 wt %, and particularly preferably 0.2 to 0.6 wt %, when the agglutination accelerator is brought into contact with the sample. When the final concentration of the agglutination accelerator is 0.1 to 5 wt %, excellent measurement sensitivity can be achieved.

(Additive)

A saccharide (e.g., glucose and sucrose), an inorganic salt (e.g., sodium chloride), a surfactant (e.g., polyoxyethylene sorbitan monostearate), a preservative (e.g., sodium azide), and/or a non-specific reaction inhibitor (e.g., IgG antibody derived from a normal animal) may be added to the reagent as long as the reaction between the anti-PSA monoclonal antibody and PSA is not hindered.

The content of the saccharide in the reagent is preferably about 0.1 to about 10 wt %, the content of the inorganic salt in the reagent is preferably about 0.01 to about 5 wt %, the content of the surfactant in the reagent is preferably about 0.02 to about 5 wt %, the content of the preservative in the reagent is preferably about 0.001 to about 0.1 wt %, and the content of the non-specific reaction inhibitor in the reagent is preferably about 0.001 to about 5 wt %.

(Buffer)

The antigen-antibody reaction according to the embodiments of the invention is effected in a buffer. The type, the concentration, and the pH of the buffer are not particularly limited as long as the antigen-antibody reaction occurs. Example of the buffer includes a phosphate buffer, a Tris-HCl buffer, a carbonate buffer, a glycine buffer, a Good's buffer, and the like. The concentration of the buffer is about 3 to about 500 mM, preferably 5 to 100 mM, and more preferably 5 to 50 mM. It is preferable that the buffer have a pH in a neutral to basic region (normally 6.5 to 9.5).

(Agglutination Signal Measurement Method)

The agglutination signal may be measured using an arbitrary method used to measure agglutination. For example, the agglutination signal may be measured by measuring the absorbance, the particle count, the particle size, scattered light, or the like.

For example, PSA is measured as described below.

Specifically, agglutination occurs when at least two kinds of antibodies that can react with both fPSA and PSA-ACT are immobilized on carriers (e.g., latex) and thereafter react with a sample that includes fPSA and/or PSA-ACT. The total PSA level in the sample can be determined by measuring the degree of agglutination, and comparing the measured degree of agglutination with the degree of agglutination when using a standard solution having a known PSA level. For example, the degree of agglutination is preferably detected as a change in absorbance by utilizing a general-purpose biochemical automatic analyzer. In this case, it is preferable to use a change in absorbance at a wavelength of 500 to 900 μm for determination of the degree of agglutination.

(Equimolar Response)

Since an equimolar response to fPSA and PSA-ACT can be obtained by utilizing the assay according to the embodiments of the invention, PSA can thereby be quantitatively determined with high accuracy.

The expression "equimolar response to fPSA and PSA-ACT" used herein means that the ratio of a signal obtained by measuring a sample that includes only fPSA to a signal obtained by measuring a sample that includes only PSA-ACT (equal mol with fPSA) is approximately 1:1.

For example, the ratio (PSA-ACT/fPSA) (hereinafter may be referred to as "c/f ratio") of agglutination signals per equal mol of fPSA and PSA-ACT is calculated, and it is considered that an equimolar response is obtained when the c/f ratio is 85 to 115% (most preferably 90 to 110%).

(Method for Producing Reagent)

The PSA assay reagent according to the embodiments of the invention is produced as described below.

Specifically, the PSA assay reagent may be produced by providing carriers having immobilized thereon two kinds of antibodies that can react with both PSA-ACT and fPSA and differ in recognition site, setting the mixing ratio of the carriers having immobilized thereon two kinds of antibodies and have an identical average particle size (more than 0.20 μm and equal to or less than 0.40 μm) within a specific range, and adjusting the concentration of the agglutination accelerator so that an equimolar response to PSA-ACT and fPSA is obtained. The mixing ratio is 1:10 to 10:1, preferably 1:5 to 5:1, and more preferably 1:2 to 2:1.

The invention is further described below by way of examples. Note that the invention is not limited to the following examples.

EXAMPLES (Preparation of Monoclonal Antibodies)

1. Immunization (1) Immunogen

Human semen-derived purified PSA (SCIPAC Ltd., Code No. P 117-7, degree of purification: 96%) was used as an immunogen. The purified PSA was used after dialysis using 20 mM PBS (pH: 7.2).

(2) Immunization Method

The above PSA solution and a complete Freund's adjuvant (CFA) (GIBCO) were mixed and emulsified in a ratio of 1:1, and administered subcutaneously to the back of 6-week-old female Balb/C mice in an amount of 25 μg PSA/mouse. Additional immunization was performed three times at intervals of 2 weeks, and the PSA solution (25 μg PSA/mouse) was administered intraperitoneally 3 days before cell fusion.

2. Cell fusion

The spleen was removed from each mouse immunized with PSA to collect spleen cells. The spleen cells and mouse myeloma cells SP2/O—Ag14 were mixed in a ratio of 6:1, and fused in the presence of 50% polyethylene glycol 1540 (Wako Pure Chemical Industries, Ltd.). The fused cells were suspended in an HAT medium so that the number of spleen cells was $2.5 \times 10^6$, and dispensed onto a 96-well culture plate (CORNING Inc.) in an amount of 0.2 ml/well. The fused cells were cultured at 37° C. for 2 weeks in a 5% $CO_2$ incubator.

3. Screening

The culture supernatant in each well of the culture plate into which the fused cells were dispensed was subjected to ELISA (see below) to select wells that reacted with both fPSA and PSA-ACT.

(1) Material: antigen

1) PSA: SCIPAC, Code No. P117-7

2) PSA-ACT: SCIPAC, Code No. P 192-3

(2) Method

1) An ELISA plate (Nunc) was coated (50 μl/well) with a goat anti-mouse IgG (Fc) antibody (Jackson Inc.) (5 μg/ml), and allowed to stand at 4° C. overnight.

2) After washing the ELISA plate with a washing solution (0.05% Tween 20-PBS) three times (400 μl/well), a blocking reagent (0.05% Tween 20-PBS) was dispensed into each well in an amount of 200 μl/well, and the ELISA plate was allowed to stand at room temperature for 1 hour.

3) After removing the blocking reagent, the culture supernatant in each well of the culture plate into which the fused cells were dispensed, was dispensed into each well of the ELISA plate in an amount of 50 µl/well, and the ELISA plate was allowed to stand at room temperature for 1 hour.
4) After washing the ELISA plate with a washing solution (0.05% Tween 20-PBS) three times, fPSA or PSA-ACT diluted with 0.05% Tween 20-PBS to 5 ng/ml was dispensed into each well in an amount of 50 µl/well, and the ELISA plate was allowed to stand at room temperature for 1 hour.
5) After washing the ELISA plate with a washing solution three times, an HRP-rabbit anti-human PSA antibody (×500) was dispensed into each well in an amount of 50 µl/well, and the ELISA plate was allowed to stand at room temperature for 1 hour. Note that the HRP-rabbit anti-human PSA antibody was prepared by a periodic acid method using a rabbit anti-human PSA antibody (DAKO) and peroxidase (Toyobo Co., Ltd.).
6) After washing the ELISA plate three times, an OPD color reagent was dispensed into each well in an amount of 50 µl/well, and the ELISA plate was allowed to stand at room temperature for 10 minutes.
7) A stop solution (1.5 N sulfuric acid) was dispensed into each well in an amount of 50 µl/well to terminate the reaction, and the absorbance at a wavelength of 492 µm was measured using a plate leader.

4. Cloning

The cell lines in the wells that reacted with both fPSA and PSA-ACT during the above screening were cloned by a limiting dilution method to establish hybridomas. 28 types of established hybridomas were thus obtained.

5. Preparation of Monoclonal Antibodies

The hybridomas ($0.5 \times 10^6$ cells) obtained by cloning were administered intraperitoneally to 8-week-old female Balb/C mice to which 0.5 ml of pristane was administered intraperitoneally 2 weeks ago. Abdominal fluid was collected when 2 weeks had elapsed, and an IgG fraction was purified using a protein A column (Amersham plc). Purified fractions of the 28 types of monoclonal antibodies were thus obtained.

(Preliminary Consideration of Combination of Monoclonal Antibodies)

Each of the 28 types of monoclonal antibodies is immobilized on a latex, and agglutination of the latex was observed as described below. Two kinds of antibodies (#91 antibody and #51 antibody) that showed a large signal, and combinations thereof with the latex were selected.

1. Selection of antibodies
(1) A 1% latex (0.3 µm) solution diluted with 20 mM Tris-HCl (pH: 8.5) and each monoclonal antibody solution (0.5 Abs) were mixed in a ratio of 1:1 (v/v), and the mixture was stirred at 4° C. for 2 hours.
(2) After the addition of 20 mM Tris-HCl (pH: 8.5) including 0.4% BSA (2 vol), the mixture was stirred at 4° C. for 1 hour.
(3) The supernatant liquid was removed by centrifugation, and suspended in 5 mM MOPS (pH: 7.0) so that the absorbance at 600 µm was 2 Abs.
(4) Two kinds of MoAb-Lx (antibody-immobilized latexes) were selected, and mixed in a ratio of 1:1 (v/v) to obtain a reagent 2 (the reagent 2 was prepared using all of the combinations).
(5) 26 ng/ml of fPSA and PSA-ACT were measured using a reagent 1 (30 mM HEPES buffer (pH: 7.0) including 0.1% BSA, 0.5 M NaCl, 0.3% polyvinylpyrrolidone K-90 (PVP K-90)) and the reagent 2 utilizing a Hitachi 7170 automatic analyzer.
(6) Two groups of antibodies that were considered to recognize different epitopes were obtained from the combinations of monoclonal antibodies that showed agglutination.
i) #63217, #63251, and #63279
ii) #63214 and #63291

Agglutination was observed using the combinations of the antibodies of groups i) and ii).

The hybridomas that produce the antibodies #63251, #63279, and #63291 are deposited at International Patent Organism Depositary (IPOD), National Institute of Advanced Industrial Science and Technology as accession numbers FERM BP-11453, FERM BP-11454, and FERM BP-11455. The monoclonal antibodies obtained from these hybridomas may be referred to as "#51 antibody", "#79 antibody", and "#91 antibody", which respectively corresponds to the first- and second-final numbers of the identification numbers.

(Production of Latexes that Differ in Particle Size)

1) 0.2 µm or less

A glass reaction vessel (2 l) equipped with a stirrer, a reflux condenser, a thermometer, a nitrogen inlet tube, a heating oil bath, and the like was charged with 1200 g of water, 200 g of a styrene monomer, 1.2 g of potassium persulfate, and 0.2 g of sodium styrene sulfonate, and the atmosphere inside the reaction vessel was sufficiently replaced with nitrogen with stirring (about 200 rpm). After polymerizing the monomer at 70° C. for about 18 hours, the reaction solution was filtered through filter paper (ADVANTEC No. 2) to obtain latex particles. The average particle size (±SD) of the latex particles was determined by photographing the latex particles using a transmission electron microscope, randomly selecting three fields of view, subjecting 100 or more latex particles within each field of view to image analysis to determine the average particle size (±SD) of the latex particles for each field of view, and averaging the average particle size (±SD) of the latex particles for each field of view. The average particle size thus determined was 0.19 µm (±0.01 µm).

2-1) 0.23 µm

Latex particles were obtained in the same manner as in section 1), except that 1200 g of water, 200 g of a styrene monomer, 2.4 g of potassium persulfate, and 0.1 g of sodium styrene sulfonate were used. The average particle size of the latex particles thus obtained was 0.23 µm (±0.01 µm).

2-2) 0.25 µm

Latex particles were obtained in the same manner as in section 1), except that 1200 g of water, 200 g of a styrene monomer, 0.9 g of potassium persulfate, and 0.2 g of sodium styrene sulfonate were used. The average particle size of the latex particles thus obtained was 0.25 µm (±0.01 µm).

2-3) 0.29 µm

Latex particles were obtained in the same manner as in section 1), except that 1200 g of water, 200 g of a styrene monomer, 1.3 g of potassium persulfate, and 0.1 g of sodium styrene sulfonate were used. The average particle size of the latex particles thus obtained was 0.29 µm (±0.01 µm).

2-4) 0.34 µm

Latex particles were obtained in the same manner as in section 1), except that 1200 g of water, 200 g of a styrene monomer, 1.3 g of potassium persulfate, and 0.08 g of sodium styrene sulfonate were used. The average particle size of the latex particles thus obtained was 0.34 µm (±0.01 µm).

2-5) 0.40 µm

Latex particles were obtained in the same manner as in section 1), except that 1200 g of water, 200 g of a styrene monomer, 1.3 g of potassium persulfate, and 0.03 g of sodium styrene sulfonate were used. The average particle size of the latex particles thus obtained was 0.40 μm (±0.01 μm).

3) More than 0.4 μm

Latex particles were obtained in the same manner as in section 1), except that 1200 g of water, 200 g of a styrene monomer, 1.2 g of potassium persulfate, and 0.01 g of sodium styrene sulfonate were used. The average particle size of the latex particles thus obtained was 0.42 μm (±0.01 μm).

(Preparation of Antibody-Immobilized Latex)

Two kinds of monoclonal antibodies (#91 and #51) obtained as described above are immobilized on carriers using the following materials and method.

1. Material
(1) Anti-PSA Monoclonal Antibody
63291 (#91)
63251 (#51)
(These Monoclonal Antibodies were Dissolved in PBS.)
(2) Latex
Polystyrene latexes (average particle size: 0.19 to 42 μm) obtained as described above 2. Preparation of Antibody-Immobilized Latex Liquid
(1) Preparation of #91 Antibody-Latex Complex (#91Lx)-Containing Liquid
1) The latex and the #91 antibody were respectively diluted with a 20 mM glycine buffer (pH: 9) to prepare a 1% latex liquid and a #91 antibody liquid (0.4 μg/ml). The latex liquid and the #91 antibody liquid were mixed (1:1, v/v), and the mixture was stirred for about 1 hour.
2) A blocking reagent (10% BSA) was added to the mixture (0.1:2, v/v), and the mixture was stirred for about 1 hour.
3) The supernatant liquid was removed by centrifugation, suspended in a 5 mM MOPS buffer (pH: 7.0), and diluted so that the absorbance at a wavelength of 600 μm was 3 Abs/ml to obtain a #91 antibody-immobilized latex (#91Lx) liquid.

PSA-ACT was determined using the following PSA measurement reagents and measurement conditions. The ratio "PSA-ACT/fPSA" (c/f ratio) of the reactivity with PSA-ACT to the reactivity with fPSA was determined. The results are shown in Table 1.

(1) PSA Measurement Reagent
First Reagent (Buffer)
30 mM HEPES buffer (pH: 7.0) including 0.5 M KCl, 0.1% BSA (Proliant), and 0.3% PVP K-90
Second Reagent (Antibody-Immobilized Latex Liquid)
5 mM MOPS buffer (pH: 7.0) including mouse anti-PSA monoclonal antibody-immobilized latex particles (mixing ratio of two kinds of antibody-immobilized particle, #91Lx-containing liquid:#51Lx-containing liquid=1:1).

Each combination of the antibody-containing liquids used in this example is prepared by respectively using latex particles having an identical average particle size (0.19 to 0.42 μm) and immobilizing thereon the #91 antibody or the #51 antibody.

(2) Measurement Conditions
Measurement system: Hitachi 7170 automatic analyzer (H-7170)
Measurement parameters:
Analysis method: 2-point end method (measurement points: 19 to 34)
Amount of liquid (μl): 14.4/90/90
Measurement wavelength (nm): 570 (main)/800 (sub)
Calibration: spline
Calibration was performed using a Nanopia (registered trademark) PSA calibrator (PSA concentration: 0, 4.2, 10, and 29 ng/ml, Sekisui Medical Co., Ltd.).

(3) Measurement Sample
The measurement samples were prepared by dissolving fPSA and PSA-ACT (Fitzgerald) in PBS (pH: 7.4) including 1% BSA and 0.1% NaN₃.

TABLE 1

| | Test Example 1-1 | Test Example 1-2 | Test Example 1-3 | Test Example 1-4 | Test Example 1-5 | Test Example 1-6 | Test Example 1-7 |
|---|---|---|---|---|---|---|---|
| Average particle size (μm) | 0.42 | 0.40 | 0.34 | 0.29 | 0.25 | 0.23 | 0.19 |
| c/f ratio (%) | 70.6 | 86.0 | 95.1 | 95.0 | 98.0 | 90.0 | 79.0 |

(2) Preparation of #51 Antibody-Latex Complex (#51Lx)-Containing Liquid
1) The latex and the #51 antibody were respectively diluted with a 20 mM Tris buffer (pH: 8) to prepare a 1% latex liquid and a #51 antibody liquid (0.4 μg/ml). The latex liquid and the #51 antibody liquid were mixed (1:1, v/v), and the mixture was stirred for about 1 hour.
2) A blocking reagent (10% BSA) was added to the mixture (0.1:2, v/v), and the mixture was stirred for about 1 hour.
3) The supernatant liquid was removed by centrifugation, suspended in a 5 mM MOPS buffer (pH: 7.0), and diluted so that the absorbance at a wavelength of 600 μm was 3 Abs/ml to obtain a #51 antibody-immobilized latex (#51Lx) liquid.

Test Example 1

(Determination of Change in c/f Ratio Due to Change in Average Particle Size of Latex)

fPSA and PSA-ACT (concentration: 5 ng/ml) were used as measurement samples, and the reactivity with fPSA and According to the results shown in Table 1, it was confirmed that the c/f ratio was 85% or more (close to 100%) and an equimolar response was obtained when the average particle size was more than 0.20 μm and equal to or less than 0.40 μm.

The c/f ratio was less than 80% and an equimolar response was not obtained when the average particle size was 0.20 μm or less, or exceeded 0.40 μm.

Test Example 2

(Adjustment of c/f Ratio by Addition of Agglutination Accelerator)

fPSA and PSA-ACT (concentration: 35 ng/ml) were used as measurement samples. The reactivity with fPSA and PSA-ACT was determined using the following PSA measurement reagents under the same measurement conditions as those employed in Test Example 1, and the ratio "PSA-ACT/fPSA" (c/f ratio) of the reactivity with PSA-ACT to the reactivity with fPSA was determined. The results are shown in Tables 2 to 4.

(1) PSA Measurement Reagent
First Reagent (Buffer)

30 mM HEPES buffer (pH: 7.0) including 0.5 M KCl, 0.1% BSA (Proliant), and 0 to 0.8% agglutination accelerator (PEG (polyethylene glycol) (the numerical value is the number average molecular weight), PVP (polyvinylpyrrolidone) (molecular weight of PVP K-30: 40,000, molecular weight of PVP K-90: 360,000, Wako Pure Chemical Industries, Ltd.), MPC polymer (molecular weight: 1,000,000), Pullulan PI-20 (molecular weight: about 200,000, Hayashibara Co., Ltd.), or PGA-Na (poly-γ-sodium glutamate) (the numerical value is the number average molecular weight) (see Tables 2 to 4))

(The Agglutination Accelerator was not Added in the Comparative Example.)

Second reagent (antibody-immobilized latex liquid)

5 mM MOPS buffer (pH: 7.0) including mouse anti-PSA monoclonal antibody-immobilized latex particles (mixing ratio of two kinds of antibody-immobilized particle, #91Lx-containing liquid:#51Lx-containing liquid=1:1).

The antibody-containing liquid used in this example is prepared by using latex having an identical average particle size (0.29 μm) and immobilizing thereon the #91 antibody and the #51 antibody.

According to the results shown in Tables 2 to 4, it was confirmed that the c/f ratio approached from about 82% to 100% due to the addition of the agglutination accelerator and an increase in the amount of the agglutination accelerator, and an equimolar response (c/f ratio: 85% or more) was obtained (showing an effect increasing the c/f ratio to about 100%) by a one-step reaction by appropriately adjusting the amount of the agglutination accelerator. Note that the term "one-step reaction" refers to adding and reacting two kinds of anti-PSA monoclonal antibodies at one time.

Test Example 3

(Determination of Reactivity Using Different Antibody Combinations)

The c/f ratio was determined using a combination of the monoclonal antibodies #79 and #91, #14 and #51, #91 and #17, or #14 and #17 instead of the combination of the monoclonal antibodies #51 and #91, and using the following measurement reagent including a 0.6% MPC polymer as the agglutination accelerator. The remaining conditions were the same as those employed in Test Example 1. fPSA and PSA-ACT (concentration: 35 ng/ml) were used as samples.

TABLE 2

|  | Comparative Example | Test Example 2-1 | Test Example 2-2 | Test Example 2-3 | Test Example 2-4 | Test Example 2-5 | Test Example 2-6 |
| --- | --- | --- | --- | --- | --- | --- | --- |
| Agglutination accelerator | Not added | PEG6000 | | | PEG20000 | | |
| Amount | — | 0.2% | 0.3% | 0.6% | 0.2% | 0.3% | 0.6% |
| c/f ratio (%) | 82.3 | 84.4 | 85.4 | 88.6 | 85.5 | 87.4 | 93.7 |

TABLE 3

|  | Test Example 2-7 | Test Example 2-8 | Test Example 2-9 | Test Example 2-10 | Test Example 2-11 | Test Example 2-12 | Test Example 2-13 |
| --- | --- | --- | --- | --- | --- | --- | --- |
| Agglutination accelerator | PVP K-30 | | | PVP K-90 | | MPC polymer | |
| Amount | 0.2% | 0.3% | 0.6% | 0.2% | 0.3% | 0.6% | 0.8% |
| c/f ratio (%) | 83.0 | 84.7 | 87.7 | 88.3 | 92.7 | 96.6 | 99.7 |

TABLE 4

|  | Test Example 2-14 | Test Example 2-15 | Test Example 2-16 | Test Example 2-17 | Test Example 2-18 | Test Example 2-19 |
| --- | --- | --- | --- | --- | --- | --- |
| Agglutination accelerator | Pullulan | | | 200,000 to 500,000 PGA-Na | 1,500,000 to 2,500,000 PGA-Na | 4,000,000 to 6,000,000 PGA-Na |
| Amount | 0.2% | 0.3% | 0.6% | 0.20% | 0.25% | 0.30% |
| c/f ratio (%) | 88.1 | 89.5 | 93.7 | 93.9 | 94.9 | 97.0 |

(1) PSA Measurement Reagent
First Reagent (Buffer)
30 mM HEPES buffer (pH: 7.0) including 0.5 M KCl, 0.1% BSA (Proliant), and 0.6% MPC polymer
The results are shown in Table 5.

TABLE 5

|  | Test Example 3-1 | Test Example 3-2 | Test Example 3-3 | Test Example 3-4 |
|---|---|---|---|---|
| Combination of antibodies | #79 antibody #91 antibody | #14 antibody #51 antibody | #91 antibody #17 antibody | #14 antibody #17 antibody |
| c/f ratio (%) | 96.4 | 89.0 | 91.2 | 101.9 |

According to the results shown in Table 5, it was confirmed that an equimolar response was obtained (c/f ratio: 89.0 to 101.9%) by using any of the above combinations.
(Kd Value of Monoclonal Antibodies Used in Test Examples)

Table 6 shows the Kd values of the monoclonal antibodies used in the test examples for fPSA and PSA-ACT. As shown in Table 6, it was confirmed that it is preferable that the anti-PSA monoclonal antibodies have a ratio (fKd/cKd) of the dissociation constant (fKd) for free PSA to the dissociation constant (cKd) for complex of free PSA and α1-antichymotrypsin (PSA-ACT) of more than 0.1 and equal to or less than 2.0, and have a dissociation constant (fKd) for free PSA of 10 nM or less.

TABLE 6

|  | Kd value (nM) | | |
|---|---|---|---|
|  | fKd | cKd | fKd/cKd |
| #14 antibody | 5.58 | 23.61 | 0.24 |
| #17 antibody | 1.72 | 4.29 | 0.40 |
| #51 antibody | 0.82 | 1.39 | 0.59 |
| #79 antibody | 0.72 | 0.57 | 1.26 |
| #91 antibody | 0.1 | 0.25 | 0.40 |

The c/f ratio was 52.4%, and an equimolar response was not obtained when using the #16 antibody (fKd=1.33 nM, cKd=23.18 nM, fKd/cKd=0.057) instead of the #91 antibody of the Test Example 3-3.

The Kd value in Table 6 was determined under the following experimental conditions.
1. Biacore (registered trademark) system and dedicated reagent (GE Healthcare (former Biacore), (i) to (viii) indicate the product name and the catalog No. from Biacore (currently available from GE Healthcare))
(i) Biacore (registered trademark) T100: JJ-1037-02 (Biacore)
(ii) Series S Sensor Chip CM5: BR-1005-30 (Biacore)
(iii) Amine Coupling Kit: BR-1000-50 (Biacore)
(iv) Acetate 5.0: BR-1003-51 (Biacore)
(v) α-Mouse Immunoglobulins: BR-1005-14 (Biacore)
(vi) Glycine 1.5: BR-1003-54 (Biacore)
(vii) Glycine 2.0: BR-1003-55 (Biacore)
(viii) HBS-EP+10×(running buffer): BR-1006-69 (Biacore) (adjusted to pH 8.5 with NaOH, and 10-fold diluted with purified water prior to use)
2. Test Method
(i) The sensor chip CM5 on which α-Mouse Immunoglobulins is immobilized is placed in the Biacore system.
(ii) The anti-PSA antibodies are respectively diluted to 1.0 µg/ml with the running buffer (HBS-EP), and added for 60 seconds at a flow rate of 30 µl/min.
(iii) The PSA antigen (fPSA or PSA-ACT) is diluted to 5.0 µg/ml with the running buffer (HBS-EP), and added for 120 seconds at a flow rate of 30 µl/min.
(iv) A free running operation is performed using the running buffer (HBS-EP) to effect dissociation for 120 seconds (flow rate: 30 µl/min)
(v) The sensor chip is regenerated using a regenerant (Glycine 1.75 prepared by mixing Glycine 1.5 and Glycine 2.0 in a ratio of 1:1).

INDUSTRIAL APPLICABILITY

The assay and the reagent according to the embodiments of the invention can easily and accurately measure PSA using a general-purpose automatic analyzer, and are useful for early detection of prostatic diseases (particularly prostate cancer).
[Reference to the deposited microorganism]
(1) FERM BP-11453 (Hybridoma #63251 producing the #51-antibody)
  i) Name and address of depository institution at which the biological materials were deposited.
  International Patent Organism Depositary, National Institute of Advanced Industrial Science and Technology Tsukuba Central 6, 1-1-1 Higashi, Tsukuba, Ibaraki 305-8566, Japan
  ii) Date of biological material deposit in the depository institution in i). Feb. 19, 2010
  iii) Accession number for the deposition assigned by the depository institution in i).
  FERM BP-11453
(2) FERM BP-11454 (Hybridoma #63279 producing the #79-antibody)
  i) Name and address of depository institution at which the biological materials were deposited.
  International Patent Organism Depositary, National Institute of Advanced Industrial Science and Technology Tsukuba Central 6, 1-1-1 Higashi, Tsukuba, Ibaraki 305-8566, Japan
  ii) Date of biological material deposit in the depository institution in i). Feb. 19, 2010
  iii) Accession number for the deposition assigned by the depository institution in i).
  FERM BP-11454
(3) FERM BP-11455 (Hybridoma #63291 producing the #91-antibody)
  i) Name and address of depository institution at which the biological materials were deposited.
  International Patent Organism Depositary, National Institute of Advanced Industrial Science and Technology Tsukuba Central 6, 1-1-1 Higashi, Tsukuba, Ibaraki 305-8566, Japan
  ii) Date of biological material deposit in the depository institution in i). Feb. 19, 2010
  iii) Accession number for the deposition assigned by the depository institution in i).
  FERM BP-11455

The invention claimed is:
1. A prostate specific antigen ("PSA") assay comprising:
  providing a mixture of insoluble carriers with two kinds of anti-PSA monoclonal antibodies respectively immobilized thereon, and
  bringing said mixture into contact with a sample in the presence of an agglutination accelerator, and thereby, reacting two kinds of anti-PSA monoclonal antibodies at one time, wherein said agglutination accelerator excludes PEG6000, wherein
the two kinds of anti-PSA monoclonal antibodies can react with both free PSA and complex of free PSA and α1-antichymotrypsin (PSA-ACT) by recognizing different epitopes,
each of the two kinds of anti-PSA monoclonal antibodies has a ratio (fKd/cKd) of a dissociation constant (fKd) for free PSA to a dissociation constant (cKd) for complex of free PSA and α1-antichymotrypsin (PSA-ACT) of more than 0.1 and equal to or less than 2.0 in the absence of said agglutination accelerator,
each of the two kinds of anti-PSA monoclonal antibodies has a dissociation constant (fKd) for free PSA of 10 nM or less,
the insoluble carriers have an identical average particle size that is more than 0.20 µm and equal to or less than 0.40 µm, and
the concentration of the agglutination accelerator has been set so that an equimolar response to free PSA and complex of free PSA and α1-antichymotrypsin (PSA-ACT) is obtained, said equimolar response obtained when c/f ratio is 90 to 115%, said c/f ratio being the ratio (PSA-ACT/fPSA) of the reactivity with PSA-ACT to the reactivity with fPSA.

2. The PSA assay according to claim 1, wherein the agglutination accelerator is one or more agglutination accelerators selected from a polysaccharide, polyvinylpyrrolidone, polyvinyl chloride, a poly-γ-glutamate, and poly(2-methacryloyloxyethylphosphorylcholine).

3. The PSA assay according to claim 1, wherein the insoluble carriers are of one or more type selected from particles comprising materials derived from latex particles of synthetic polymers, silica, alumina, carbon blacks, metal compounds, metals, ceramics, and/or magnetic substances.

4. The PSA assay according to claim 2, wherein the polysaccharide is one or more polysaccharides selected from dextran, pullulan, and alkylated polysaccharides.

5. The PSA assay according to claim 3, wherein the synthetic polymer is one or more synthetic polymers selected from polystyrene, a styrene-sulfonic acid copolymer, a styrene-methacrylic acid copolymer, an acrylonitrile-butadiene-styrene copolymer, a vinyl chloride-acrylate copolymer, and a vinyl acetate-acrylate copolymer.

6. The PSA assay according to claim 4, wherein the polysaccharide is methyl cellulose and/or ethyl cellulose.

7. A prostate specific antigen ("PSA") assay comprising:
contacting a sample with a Reagent A to form a mixture, said Reagent A including a mixture of insoluble carriers with two kinds of anti-PSA monoclonal antibodies respectively immobilized thereon, and thereby, reacting two kinds of anti-PSA monoclonal antibodies at one time, and wherein
the two kinds of anti-PSA monoclonal antibodies can react with both free PSA and complex of free PSA and α1-antichymotrypsin (PSA-ACT) and recognize different epitopes,
each of the two kinds of anti-PSA monoclonal antibodies has a ratio (fKd/cKd) of a dissociation constant (fKd) for free PSA to a dissociation constant (cKd) for complex of free PSA and α1-antichymotrypsin (PSA-ACT) of more than 0.1 and equal to or less than 2.0 in the absence of said agglutination accelerator,
each of the two kinds of anti-PSA monoclonal antibodies has a dissociation constant (fKd) for free PSA of 10 nM or less, and
the insoluble carriers have an identical average particle size that is more than 0.20 µm and equal to or less than 0.40 µm; and
reacting the mixture of the sample and Reagent A with a Reagent B, said Reagent B including one or more agglutination accelerators selected from polyethylene glycol, a polysaccharide, polyvinylpyrrolidone, polyvinyl chloride, a poly-γ-glutamate, and poly(2-methacryloyloxyethylphosphorylcholine), wherein said agglutination accelerator excludes PEG6000,
wherein the concentration of the agglutination accelerator has been set so that an equimolar response to free PSA and complex of free PSA and α1-antichymotrypsin (PSA-ACT) is obtained, said equimolar response obtained when c/f ratio is 90 to 115%, said c/f ratio being the ratio (PSA-ACT/fPSA) of the reactivity with PSA-ACT to the reactivity with fPSA.

8. The PSA assay according to claim 7, wherein the insoluble carriers are of one or more type selected from particles comprising materials derived from latex particles of synthetic polymers, silica, alumina, carbon blacks, metal compounds, metals, ceramics, and/or magnetic substances.

9. The PSA assay according to claim 8, wherein the synthetic polymer is one or more synthetic polymers selected from polystyrene, a styrene-sulfonic acid copolymer, a styrene-methacrylic acid copolymer, an acrylonitrile-butadiene-styrene copolymer, a vinyl chloride-acrylate copolymer, and a vinyl acetate-acrylate copolymer.

10. The PSA assay according to claim 7, wherein the polysaccharide is one or more polysaccharides selected from dextran, pullulan, and alkylated polysaccharides.

11. The PSA assay according to claim 10, wherein the alkylated polysaccharides are methyl cellulose and/or ethyl cellulose.

* * * * *